US009788727B2

(12) United States Patent
Narusawa (10) Patent No.: US 9,788,727 B2
(45) Date of Patent: *Oct. 17, 2017

(54) PHYSIOLOGICAL INFORMATION MEASURING APPARATUS (71) Applicant: Seiko Epson Corporation, Shinjuku-ku (JP)

(72) Inventor: Atsushi Narusawa, Chino (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/388,085

(22) Filed: Dec. 22, 2016

(65) Prior Publication Data

US 2017/0100038 A1    Apr. 13, 2017

Related U.S. Application Data (63) Continuation of application No. 14/463,519, filed on Aug. 19, 2014, now Pat. No. 9,560,971.

(30) Foreign Application Priority Data

Aug. 22, 2013 (JP) ................. 2013-172398

(51) Int. Cl.
*A61M 5/00* (2006.01)
*A61B 5/11* (2006.01)
(Continued)

(52) U.S. Cl.
CPC .......... *A61B 5/0059* (2013.01); *A61B 5/0205* (2013.01); *A61B 5/11* (2013.01);
(Continued)

(58) Field of Classification Search
CPC ... A61B 5/0059; A61B 5/0205; A61B 5/6843; A61B 5/681; A61B 5/742; A61B 5/021
See application file for complete search history.

(56) References Cited

U.S. PATENT DOCUMENTS 4,796,636 A * 1/1989 Branstetter ........ G01N 21/3151
356/42
5,057,695 A * 10/1991 Hirao ................. A61B 5/14551
250/575
(Continued)

FOREIGN PATENT DOCUMENTS

EP    0 941 694 A1    9/1999
EP    2 016 890 A2    1/2009
(Continued)

OTHER PUBLICATIONS

Groothuis, Jan, et al., "Venous cuff pressures from 30mmHg to diastolic pressure are recommended to measure arterial inflow by plethysmography," Journal of Applied Physiology, pp. 342-347, (Apr. 4, 2003).
(Continued)

*Primary Examiner* — Sang Nguyen
(74) *Attorney, Agent, or Firm* — Kilpatrick Townsend & Stockton LLP (57) ABSTRACT A physiological information measuring apparatus includes a first detection unit, having a first light emitting unit and a first light receiving unit, separated from one another by a first distance. A second detection unit of the physiological information measuring apparatus has a second light emitting unit and a second light receiving unit, separated from one another by a second, different distance. Alternatively, the second detection unit shares the first light emitting unit with the first detection unit and has a second light receiving unit. Alternatively, the second detection unit shares the first light receiving unit with the first detection unit and has a second light emitting unit. A measuring unit of the physiological information measuring apparatus measures the physiological information of a user based on light received by the light receiving unit or light receiving units.

14 Claims, 5 Drawing Sheets (51) Int. Cl.
*A61B 5/0205* (2006.01)
*A61B 5/00* (2006.01)
*A61B 5/021* (2006.01)
*A61B 5/024* (2006.01)
*A61B 5/08* (2006.01)

(52) U.S. Cl.
CPC ............ *A61B 5/681* (2013.01); *A61B 5/6843* (2013.01); *A61B 5/742* (2013.01); *A61B 5/021* (2013.01); *A61B 5/02416* (2013.01); *A61B 5/0816* (2013.01)

(56) References Cited

U.S. PATENT DOCUMENTS

| | | | |
|---|---|---|---|
| 5,188,108 A | 2/1993 | Secker | |
| 5,277,181 A * | 1/1994 | Mendelson | A61B 5/14551 356/41 |
| 5,285,783 A * | 2/1994 | Secker | A61B 5/04485 356/41 |
| 5,524,617 A | 6/1996 | Mannheimer | |
| 5,734,464 A | 3/1998 | Gibbs | |
| 5,787,887 A | 8/1998 | Klingenbeck-Regn | |
| 5,983,122 A * | 11/1999 | Jarman | A61B 5/0059 356/41 |
| 6,657,183 B2 | 12/2003 | Yamamoto et al. | |
| 7,060,963 B2 | 6/2006 | Maegawa et al. | |
| 7,130,672 B2 * | 10/2006 | Pewzner | A61B 5/14553 600/310 |
| 7,304,724 B2 | 12/2007 | Durkin et al. | |
| 8,725,226 B2 | 5/2014 | Isaacson | |
| 8,923,942 B2 * | 12/2014 | Bernreuter | A61B 5/14551 600/323 |
| 2002/0033454 A1 * | 3/2002 | Cheng | A61B 5/14546 250/339.12 |
| 2003/0007161 A1 | 1/2003 | Bowles | |
| 2004/0193063 A1 | 9/2004 | Kimura et al. | |
| 2007/0167844 A1 | 7/2007 | Asada et al. | |
| 2014/0051941 A1 | 2/2014 | Messerschmidt | |
| 2014/0288885 A1 | 9/2014 | Morita | |

FOREIGN PATENT DOCUMENTS

| | | |
|---|---|---|
| EP | 2 016 890 A3 | 1/2009 |
| JP | 55-120858 A | 9/1980 |
| JP | 2003-528645 A | 9/2003 |
| JP | 2004-261366 A | 9/2004 |
| JP | 2005-323906 A | 11/2005 |
| JP | 2007-330708 A | 12/2007 |
| JP | 2013-116210 A | 6/2013 |
| WO | 00/64338 A2 | 11/2000 |
| WO | 2012/110955 A1 | 8/2012 |

OTHER PUBLICATIONS

Extended European search report, dated Jan. 21, 2015, of the corresponding European Application No. 14181585.2; (seven pages).

Non-Final Office Acton dated Jun. 2, 2016 in related U.S. Appl. No. 14/463,519 (17 pages).

* cited by examiner

PHYSIOLOGICAL INFORMATION MEASURING APPARATUS

CROSS REFERENCE TO RELATED APPLICATIONS

This application is a continuation of U.S. patent application Ser. No. 14/463,519, filed Aug. 19, 2014, which claims priority to Japanese Patent Application No. 2013-172398, filed Aug. 22, 2013, the disclosure of which is incorporated herein by reference.

BACKGROUND

1. Technical Field

The present invention relates to an apparatus for measuring a user's physiological information, such as a heart rate.

2. Related Art

Since a heartbeat manifests itself as a pulse, i.e. a change of volume of blood, it is possible to measure the heart rate using a photoelectric pulse sensor that detects a change in blood volume at a site on a user's body, e.g. a wrist. However, the volume of blood also changes depending on body movements in addition to heartbeats. For this reason, when measuring the heart rate using a photoelectric pulse sensor, noise caused by the body movement is included in the process of transmission of the blood from the heart to the wrist. That is, since blood is a fluid and the blood vessels are elastic, the flow of blood generated by body movements causes a change in an amount of blood, the flow being measured as a pseudo-pulsation.

A heart rate monitor that accounts for a noise component due to body movements is disclosed in JP-A-55-120858, which is incorporated by reference herein. Light beams with different wavelengths are transmitted, reflected, and measured. Pulsation components are calculated from the measured values. The method uses the fact that oxygenated hemoglobin (which is dominant in arterial blood) and reduced hemoglobin (which is dominant in venous blood) have different light absorption characteristics.

However, the light beams of different wavelengths also penetrate the user's skin to different depths. This causes additional noise, making it difficult to remove the noise caused by the body movement.

SUMMARY

A physiological information measuring apparatus includes a first detection unit, having a first light emitting unit and a first light receiving unit, separated from one another by a first distance. A second detection unit of the physiological information measuring apparatus has a second light emitting unit and a second light receiving unit, separated from one another by a second, different distance. A measuring unit of the physiological information measuring apparatus measures the physiological information of a user based on light received by the first light receiving unit and by the second light receiving unit.

The detection units may be disposed on an exposed surface of the apparatus and configured to contact the user's skin during use.

The first light emitting unit and the second light emitting unit may emit light with the same wavelength as one another. The wavelength(s) may be 470 nm to 610 nm.

The light receiving units may apply pressure to the user's skin. Each light receiving unit may apply the same amount of pressure. Each light receiving unit may apply the pressure in an amount from 1 kPa to 6 kPa, from 2 kPa to 3 kPa, or from 5 kPa to 6 kPa.

The first distance may be from 2 mm to 4 mm, and the second distance may be from 4 mm to 10 mm.

A first region from the first light emitting unit to the first light receiving unit along the surface of the apparatus may overlap a second region from the second light emitting unit to the second light receiving unit along the surface of the apparatus.

The measuring unit may measure the physiological information by removing noise, where the noise can be measured based on differences between the light received by the first light receiving unit and the light received by the second light receiving unit.

The physiological information may be at least one of: the user's heart rate, the user's blood pressure, the user's breathing rate, and the user's autonomic balance.

BRIEF DESCRIPTION OF THE DRAWINGS

Exemplary embodiments of the invention will be described with reference to the accompanying drawings, wherein like numbers reference like elements.

DESCRIPTION OF EXEMPLARY EMBODIMENTS

1. Embodiment

1-1. Overall Configuration

Figure 1:
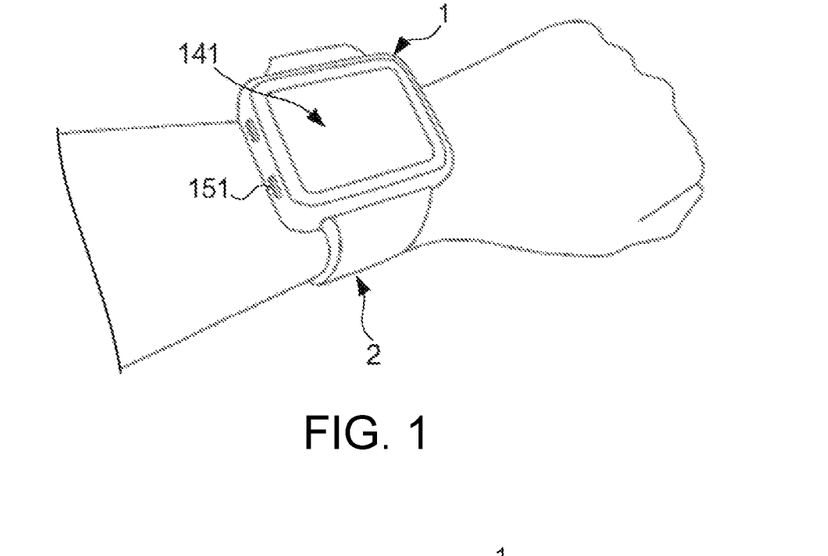
FIG. 1 is a view showing the appearance of an exemplary heart rate monitor.

FIG. 1 is a view showing the appearance of a physiological information measuring apparatus, exemplified as a heart rate monitor 1. The heart rate monitor 1 has a configuration resembling a wristwatch which is worn on the wrist of a user using a wrist band 2. A front surface of the heart rate monitor 1 is provided with a display surface 141 (to be described later) formed of a liquid crystal panel or the like, and a side surface of the heart rate monitor 1 is provided with an input element 151 (to be described later) such as one or more buttons and/or switches which is pressed by the user for operation. A back surface of the heart rate monitor 1 contacts the skin on the user's wrist.

Figure 2:
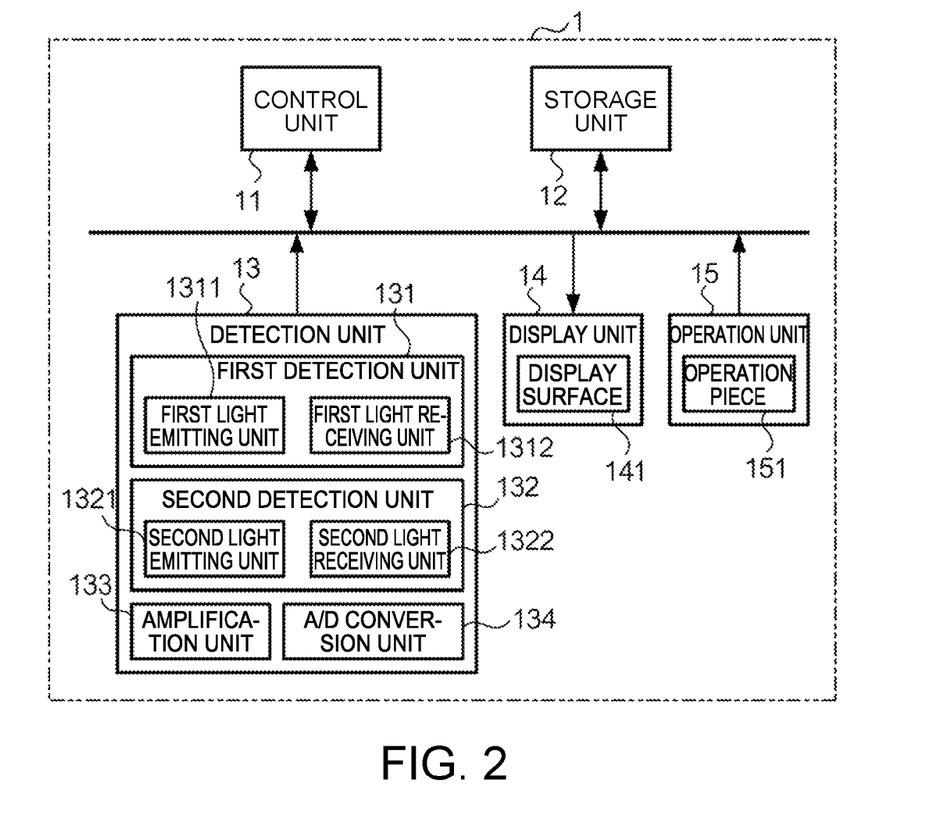
FIG. 2 is a block diagram of the heart rate monitor of FIG. 1.

FIG. 2 is a block diagram of the heart rate monitor 1. A control unit 11 has a central processing unit (CPU), a read only memory (ROM), and a random access memory (RAM), and controls each unit of the heart rate monitor 1 by the CPU executing to read a computer program (hereinafter, simply referred to as program) stored in the ROM or a storage unit 12.

The storage unit 12 is a large capacity storage unit such as a solid state drive (SSD) and stores the program read by the CPU. A display unit 14 includes the display surface 141 and causes the display surface 141 to display images and/or text according to an instruction from the control unit 11.

An operation unit 15 includes the input element 151 for performing various instructions and receives input from the user to supply a signal corresponding to the input to the control unit 11. The input element 151 may include one or more buttons and/or switches, and/or a transparent touch panel which overlaps the display surface 141.

A detection unit 13 has a first detection unit 131 and a second detection unit 132. The first detection unit 131 is configured to measure the user's heart rate and to output a first signal that represents the heart rate. Specifically, the first detection unit 131 has a first light emitting unit 1311 and a first light receiving unit 1312 which contact the skin surface of the wrist during use. The first light emitting unit 1311 irradiates the inside of the user's body with light having a particular wavelength.

The second detection unit 132 is configured to measure the user's heart rate at a sensitivity different from the first detection unit 131 and to output a second signal that represents the heart rate. Here, the "sensitivity" is a noise sensitivity, i.e. a ratio of a noise component of a signal to a component that is actually indicative of the heart rate. Specifically, the second detection unit 132 has a second light emitting unit 1321 and a second light receiving unit 1322 which contact the surface of the user's skin during use. The second light emitting unit 1321 irradiates the inside of the user's body with light having a particular wavelength. The difference in the sensitivities between the above-described first detection unit 131 and the second detection unit 132 can be derived from the difference between the distance between the first light emitting unit 1311 and the first light receiving unit 1312, and the distance between the second light emitting unit 1321 and the second light receiving unit 1322.

The detection unit 13 also includes an amplification unit 133, i.e. an amplifier that amplifies signals which are respectively output from the first detection unit 131 and the second detection unit 132, and an A/D conversion unit 134, which converts an analog signal amplified by the amplification unit 133 into a digital signal.

Figure 3A:
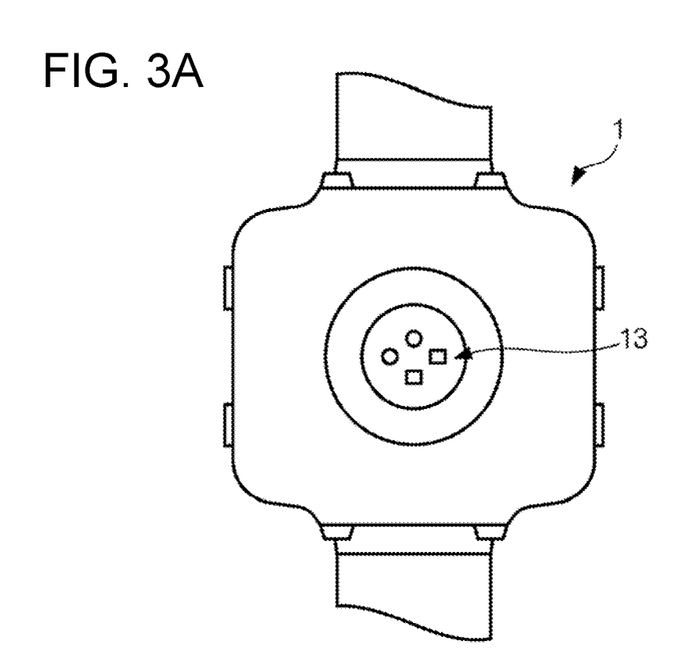
FIGS. 3A and 3B show the side of the heart rate monitor of FIGS. 1 and 2 that faces a user's skin, with FIG. 3B showing an enlarged portion of FIG. 3A.
Figure 3B:
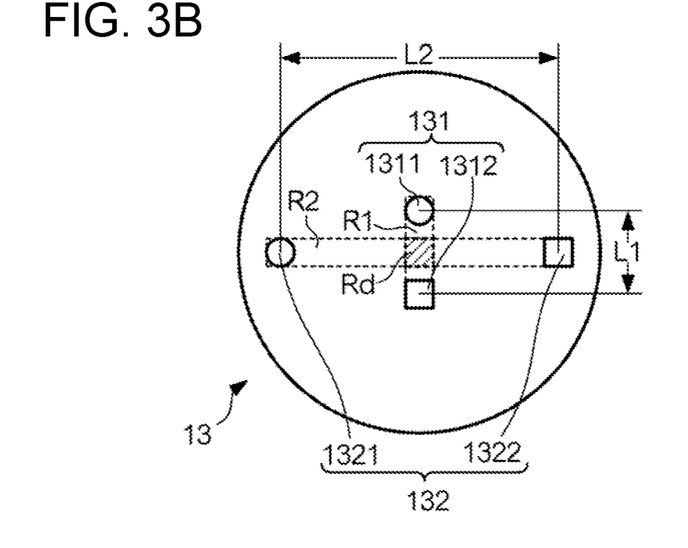

FIGS. 3A and 3B show the detection unit 13 in more detail. As shown in FIG. 3A, the detection unit 13 is disposed on a back surface (that is, a surface opposite to the display surface 141 of the heart rate monitor 1) so as to contact the skin of the user's wrist.

As shown in more detail in FIG. 3B, the first light emitting unit 1311 and the first light receiving unit 1312 of the first detection unit 131, and the second light emitting unit 1321 and the second light receiving unit 1322 of the second detection unit 132 are disposed on the back surface of the monitor 1 and contact the user's skin. The distance L1 between the first light emitting unit 1311 and the first light receiving unit 1312 is shorter than the distance L2 between the second light emitting unit 1321 and the second light receiving unit 1322, where the distances are measured along the skin surface of the user's wrist.

The first light receiving unit 1312 presses a first site on the user's wrist at a certain pressure (which will be described later) and receives light from the first light emitting unit 1311 reflected from the inside of the user's body, through the first site.

The second light receiving unit 1322 presses a second, different site on the user's wrist at the same pressure and receives the light from the second light emitting unit 1321 reflected from the inside of the user's body through the second site.

A first region R1 from the first light emitting unit 1311 and the first light receiving unit 1312 on the skin surface intersects a second region R2 from the second light emitting unit 1321 to the second light receiving unit 1322 on the skin surface at an overlapping region Rd. As such, that there is an overlapping portion Rd of the light passages of the first detection unit 131 and the second detection unit 132. In other words, each light passage permeates a common portion Rd of the user. Accordingly, both the first detection unit 131 and the second detection unit 132 detect the heart rate in the common portion Rd, and therefore, there are fewer errors than in cases in which the first region R1 does not overlap with the second region R2. In particular, because the first region R1 intersects the second region R2, positions at which the light beams respectively received by the first light receiving unit 1312 and the second light receiving unit 1322 are reflected are very near each other, as will be described later with reference to FIG. 4. Alternatively, the light beams may be side-by-side or otherwise near, but not intersecting, each other. However, these embodiments may not be quite as accurate, as will become clear from the description of FIG. 4.

The first light emitting unit 1311 irradiates the user's tissue with light which has a certain wavelength and has an intensity corresponding to an electric current supplied from a power source (not shown). The wavelength is, for example, approximately 470 nm to approximately 610 nm, and more preferably, approximately 520 nm to approximately 570 nm. These wavelengths have been selected because they are more easily reflected from hemoglobin in the blood vessels than other wavelengths. The first light receiving unit 1312 receives some of the light from the first light emitting unit 1311, which is reflected from a certain depth in the tissue and outputs a first signal corresponding to the intensity of the received light. The reflected light includes various elements. Among them, the light reflected from the hemoglobin in the blood vessels represents the heart rate. The reflected light is also influenced by body movement of the user, and thus, the reflected light often includes noise.

The second light emitting unit 1321 irradiates the user's tissue with light which has the same wavelength as the first light emitting unit 1311 and has an intensity corresponding to the supplied electric current. The second light receiving unit 1322 receives some of the light reflected from the tissue from the second light emitting unit 1321 and outputs a second signal corresponding to the intensity of the received light.

Figure 4:
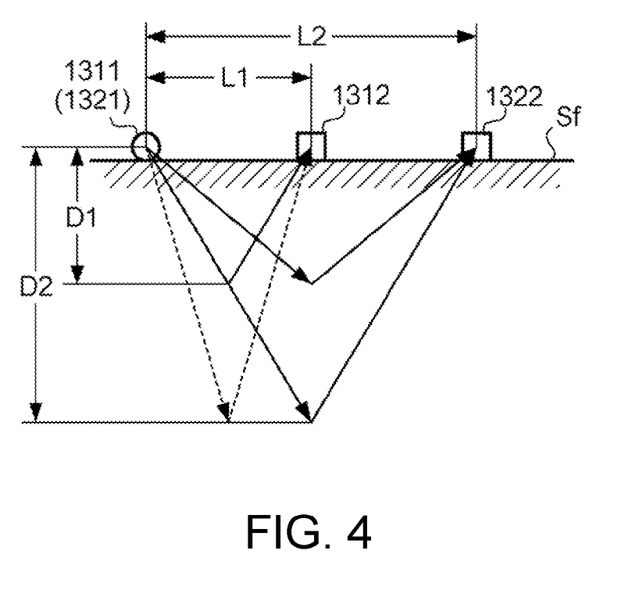
FIG. 4 schematically illustrates the influence of the distance between a light emitting unit and a light receiving unit on the penetration depth of light.

FIG. 4 shows the geometry of the distances between the light emitting units and the light receiving units, and the penetration depths of light. A skin face Sf of the wrist of the user contacts the first light emitting unit 1311, the first light receiving unit 1312, the second light emitting unit 1321, and the second light receiving unit 1322. In FIG. 4, the first light emitting unit 1311 is illustrated at the same position as the second light emitting unit 1321, for purposes of simplification and illustration.

It is found that the shorter the distance between the light emitting unit and the light receiving unit, the more the sensitivity depends on depth. That is, the intensity of light radiated from the first light emitting unit 1311, the light being reflected at a position having a depth D1 in the user's tissue and reaching the first light receiving unit 1312, is stronger than the intensity of light which is reflected at a position having a depth D2 deeper than the depth D1 and reaches the first light receiving unit 1312. Similarly, the intensity of light radiated from the second light emitting unit 1321, the light being reflected at a position having the depth D1 and reaching the second light receiving unit 1322, is stronger than the intensity of light which is reflected at the position having the depth D2 and reaches the second light receiving unit 1322. However, the difference in the second case is not as pronounced as in the first detection unit 131. For this reason, the first detection unit 131 is configured to be suitable for detecting light reflected at a site comparatively shallow to that of the second detection unit 132.

Figure 5:
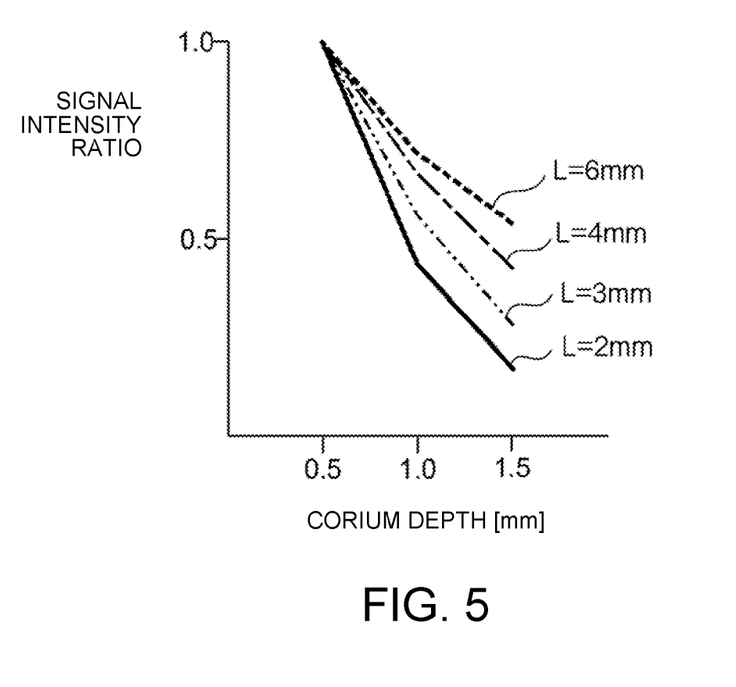
FIG. 5 is a view showing a relationship between the penetration depth and a signal intensity ratio for several distances between the light emitting unit and the light receiving unit.

FIG. 5 shows the relationship between the depth at which light is reflected and a signal intensity ratio for several distances L. FIG. 5 shows the ratio of the signal intensity of light beams respectively reflected from positions having 1.0 mm depth of the corium and 1.5 mm depth of the corium, normalized to a signal intensity of 1 for light which is reflected at a position having 0.5 mm depth of the corium. For example, in a case where the distance L from the light emitting unit to the light receiving unit is 2 mm, the signal intensity of light reflected at 1.5 mm depth of the corium is about 20% of the signal intensity of light reflected at the position having 0.5 mm of the depth of the corium. However, in a case where the distance L is 6 mm, the signal intensity maintains about 55%. That is, the longer the distance L, the easier the detection of the reflected light by the detection unit 13 at a relatively deeper position. Therefore, the differences of the sensitivities of light beams respectively reflected from a shallow position and a deep position are reduced. While the distance the light beam travels within the skin is easily found with elementary geometry, the signal intensity is not a direct inverse correlation to this distance, and these numbers have only been found experimentally. Why this is the case is not known for certain, but based on speculation, perhaps the tissue in the different layers of the corium has different resistance to light at the appropriate wavelengths.

Figure 6A:
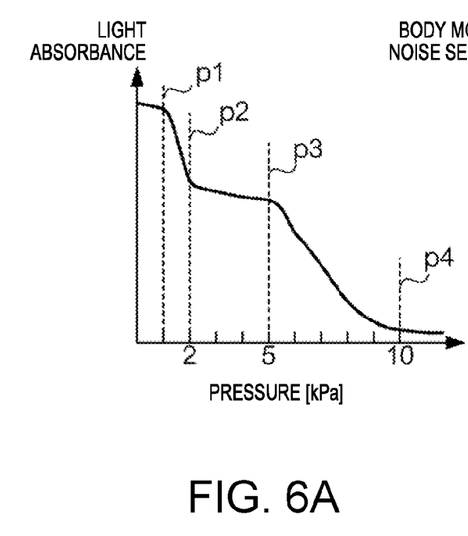
FIGS. 6A and 6B are views showing light absorbance and body movement noise sensitivity, respectively, as a function of pressure applied to the user's skin.
Figure 6B:
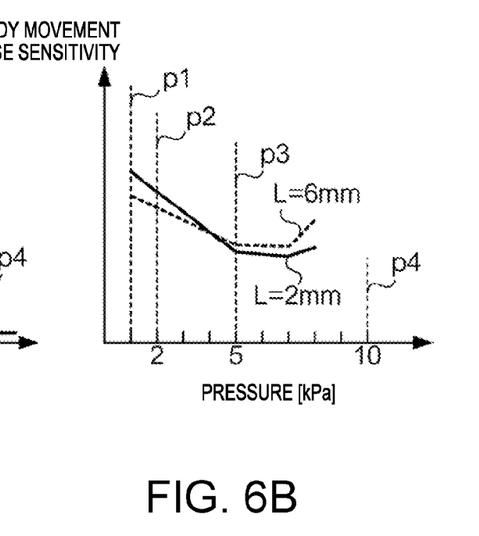

FIGS. 6A and 6B are views showing the relationship between light absorbance and body movement noise sensitivity, respectively, with respect to applied pressure. The pressure on the contact surface can be applied at a desired amount by the detection unit 13. It will be appreciated that the dermis layer has many capillaries and is a soft tissue, and therefore, is easily compressed at a low pressure. The capillary relaxation pressure p1 shown in FIG. 6A is a critical pressure at which the capillaries start to be closed when the pressure exceeds p1, and the capillary closure pressure p2 shown in FIG. 6A is a critical pressure at which the capillaries are completely closed when the pressure exceeds p2. In addition, when the pressure exceeds the artery relaxation pressure p3 shown in FIG. 6A, the arteries start to be closed, and when the pressure exceeds the artery closure pressure p4, the arteries are completely closed.

If the pressure at which the detection unit 13 of the heart rate monitor 1 presses the surface of the user's skin is between the capillary relaxation pressure p1 and the capillary closure pressure p2, the capillaries are partially, but not completely, closed. Accordingly, in this case, blood flowing in the capillaries is easily moved by body movement. Therefore, light which is reflected from the capillaries at a comparatively shallow position in the tissue tends to include noise. As a result, the reflected light in the shallow position is easily detected in a configuration in which the distance L from the light emitting unit to the light receiving unit is 2 mm, compared to a configuration in which the distance L is 6 mm which is longer than 2 mm. Thus, the sensitivity with respect to the noise caused by the body movement (that is, body movement noise sensitivity) is high in the configuration in which the distance L is 2 mm.

In contrast, if the pressure force is set within a range of the artery relaxation pressure p3 to the artery closure pressure p4, since the artery relaxation pressure p3 is a higher pressure than the capillary closure pressure p2, the capillaries enter a state of being closed completely and the arteries enter a state of not being closed completely. Accordingly, in this case, blood inside of the capillaries hardly moves since the capillaries are pressed. That is, light reflected from the tissue of the living body at a comparatively shallow position at which the capillaries exist hardly includes noise. However, since the arteries are not completely closed, blood inside of the arteries easily moves. That is, light reflected from the tissue of the living body at a relatively deep position at which the arteries exist tends to include noise. As a result, the reflected light in the deep position is easily detected in the configuration with 6 mm of the distance L compared to the configuration with 2 mm of the distance L. Thus, the body movement noise sensitivity is high in the configuration with 6 mm of the distance L.

In other words, when L is 2 mm, the signal is much weaker at depth. Therefore, most of the signal comes from the higher layers, where capillaries are dominant and arteries are scarce. Thus, for p1<p<p2, there will be a high amount of noise. However, if the capillaries are completely closed, for p3<p<p4, there will be a low amount of noise.

When L is 6 mm, on the other hand, the signal is not much weaker at depth. Thus, more of the signal comes from the lower layers, where arteries are dominant and capillaries are scarce. Thus, there will be a lower amount of noise than for the previous case at p1<p<p2, and a higher amount of noise than for the previous case at p3<p<p4.

These effects are quantified in FIG. 6B.

As such, the body movement noise sensitivity of the first detection unit 131 (with distance L1) and the body movement noise sensitivity of the second detection unit 132 (with distance L2) are reversed to each other depending on what range the pressure is set to. In other words, one exhibits relatively high noise and one exhibits relatively lower noise at each pressure. For example, in the example shown in FIGS. 6A and 6B, if the pressure at which the skin is pressed is between 2 kPa to 3 kPa, the body movement noise sensitivity of the first detection unit 131 is higher than that of the second detection unit 132. It is believed that this is because the arteries are released and the capillaries tend to include more body movement noise than the arteries, since the pressure within the range of 2 kPa to 3 kPa is lower than the artery relaxation pressure p3. Since the pressure in the range of 2 kPa to 3 kPa is relatively low, the risk is low of inflicting pain or discomfort on the user compared to other configurations even when continuously measuring the heart rate over a comparatively long period of time, for example, for several days.

In contrast, if the pressure at which the skin is pressed is between 5 kPa to 6 kPa, the body movement noise sensitivity of the second detection unit 132 is higher than that of the first detection unit 131. The program stored in the storage unit 12 is written so that the control unit 11 specifies which body movement noise sensitivity (i.e. either the first detection unit 131 or the second detection unit 132) is higher, depending on the applied pressure.

1-2. Functional Configuration of Control Unit

Figure 7:
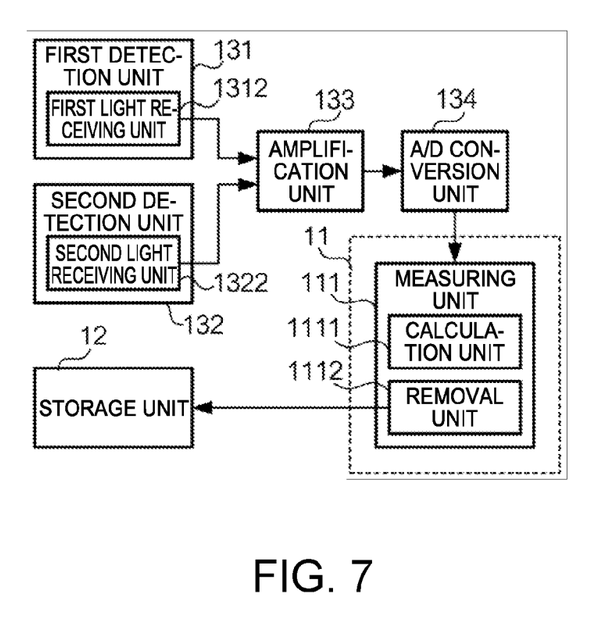
FIG. 7 is a block diagram of a control unit.

FIG. 7 schematically illustrates the control unit 11 along with its inputs and outputs. The first signal output from the first light receiving unit 1312 of the first detection unit 131 and the second signal output from the second light receiving unit 1322 of the second detection unit 132 are respectively amplified via the amplification unit 133, converted into a digital signal by the A/D conversion unit 134, and then supplied to the control unit 11. That is, the control unit 11 acquires the first signal, which represents the heart rate, from the first detection unit 131. In addition, the control unit 11 acquires the second signal, which represents the heart rate, from the second detection unit 132, whose noise sensitivity is different than the first detection unit 131.

The control unit 11 functions as a measuring unit 111 that measures the heart rate based on both of the signals. The measuring unit 111 has a calculation unit 1111 that calculates the differences in the frequencies of the first signal and the second signal, and a removal unit 1112 that removes noise caused by body movement from any one of the first signal and the second signal based on the differences of the frequencies calculated by the calculation unit 1111. The measuring unit 111 measures the heart rate by extracting body movement noise from the signal output from the detection unit that has the higher body movement noise sensitivity and by removing the body movement noise from the signal output from the detection unit that has the lower body movement noise sensitivity. The numerical value that represents the measured heart rate is stored in the storage unit 12.

As described above, in the two detection units having light emitting units respectively radiating light beams having the same wavelength, the heart rate monitor 1 can measure the heart rate with high accuracy compared to previously known monitors, since noise included in the signals is removed using the different distances from the light emitting units to the respective light receiving units. In other words, by applying a single constant pressure, the monitor can assume that any differences in the heart rates measure by the two detection units 131 and 132 is a result of noise caused by body movement. Knowing the relative noise levels for the two units 131 and 132 for the given pressure allows the monitor to isolate the noise signals and subtract them from the signals to give an accurate reading.

2. Modifications

An exemplary embodiment has been described above, but can be modified in many ways, some of which are set forth below. In addition, features from different embodiments may also be combined together.

2-1. Modification 1

Figure 8A:
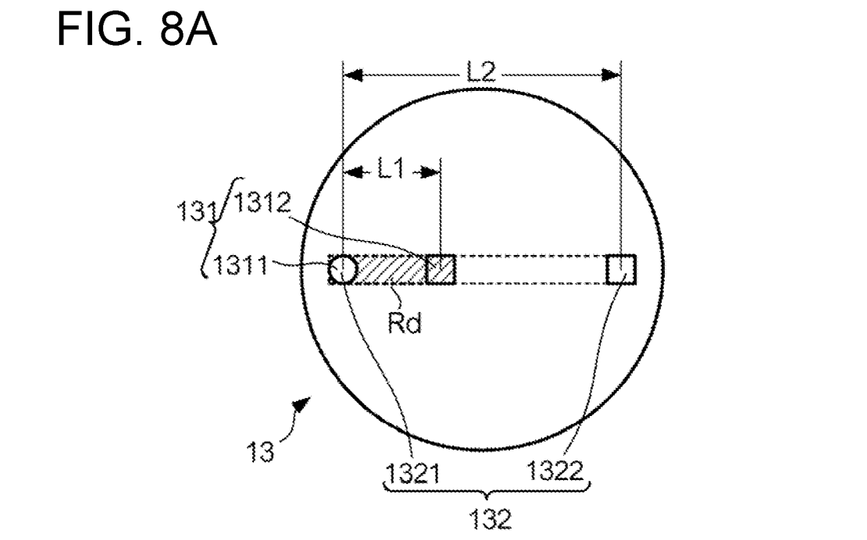
FIGS. 8A and 8B are views similar to FIG. 3B, showing alternative exemplary embodiments.
Figure 8B:
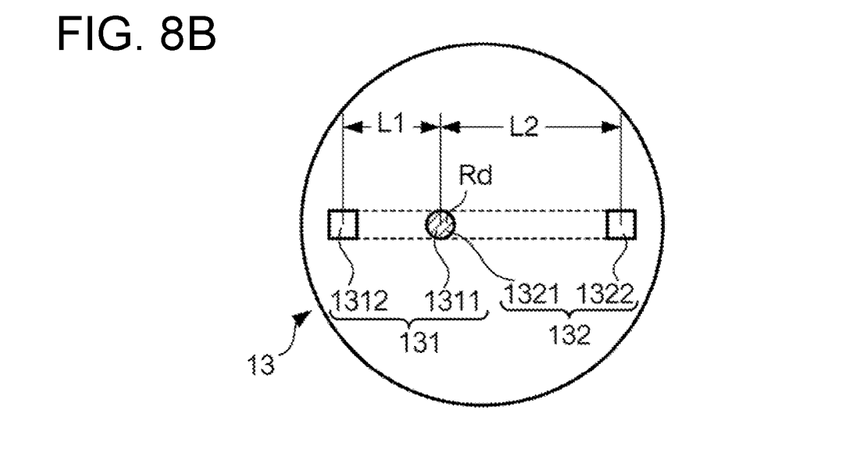

Although the first region R1 intersects the second region R2 in the first embodiment, the disposition of the regions is not limited thereto. In addition, although the first embodiment includes two light emitting units 1311 and 1321, a single light emitting unit may serve as both. FIGS. 8A and 8B show alternative exemplary configurations of a light emitting unit and light receiving units. The first light emitting unit 1311 serves as the second light emitting unit 1321 as shown in FIG. 8A. The second light receiving unit 1322 is provided in the same direction as the first light receiving unit 1312. That is, the first region R1 from the light emitting unit 1311 to the first light receiving unit 1312 may be a subset of the second region R2 from the light emitting unit 1321 to the second light receiving unit 1322.

2-2. Modification 2

Alternatively, as shown in FIG. 8B, a single light emitting unit may serve as both light emitting units 1311 and, 1321 and the second light receiving unit 1322 may be provided in an opposite direction than the first light receiving unit 1312 from the light emitting unit 1311, 1321. In this case, only the region of the light emitting unit 1311, 1321 is the overlapping region Rd.

2-3. Modification 3

In the first embodiment, the control unit 11 isolates the noise signals based on the differences of the two frequencies. However, the control unit 11 may instead use the differences in intensity (i.e. amplitude) or other parameters.

2-4. Modification 4

In the first embodiment, the pressure applied by the detection unit 13 is constant, but the invention is not limited thereto. In cases in which the pressure is not constant, the heart rate monitor 1 may further include a pressure monitor and the control unit 11 may specify which body movement noise sensitivity is higher for each possible pressure.

2-5. Modification 5

The number of detection units is not limited to two, but may be three or more. In these cases, the heart rate monitor 1 may acquire two heart rate signals using signals output from two of the three or more detection units.

2-6. Modification 6

In a presently preferred embodiment, the first distance L1 is 2 mm to 4 mm, and the second distance L2 is 4 mm to 10 mm.

2-7. Modification 7

The example illustrated in FIGS. 6A and 6B shows that the body movement noise sensitivity of the first detection unit 131 is higher than that of the second detection unit 132 if the pressure is 2 kPa to 3 kPa, and the body movement noise sensitivity of the second detection unit 132 is higher than that of the first detection unit 131 if the pressure is 5 kPa to 6 kPa. However, the pressure is not limited to the range. In a presently preferred embodiment, the pressure is 1 kPa to 6 kPa. This range strikes a balance between causing discomfort or annoyance, and detection accuracy.

While a heart rate monitor has been described herein as one exemplary embodiment of a physiological information measuring apparatus, the instant invention is not limited thereto.

The measuring apparatus described herein can measure not only the user's heart rate, but the user's pulse wave, from which many physiological parameters can be derived, such as, for example and without limitation, blood pressure, breathing rate, autonomic balance, etc.

As will be understood by those of ordinary skill in the art, the pulse wave (PW) is a complex physiological phenomenon observed and detected in blood circulation. In the cardiac systole, a specified volume of blood is ejected and it moves in arteries due to transformation of the potential and kinetic energy of the ejected blood. In an artery or in a vein where the pulse wave is propagating, three dependable phenomena can be observed: blood streaming (streaming pulse), the increase of blood pressure (pressure pulse) and distension of the transverse profile (profile or volume pulse). The PW shape varies in different parts of circulation. It depends on physiological or pathophysiological conditions of the organism. To the physiological factors the heart rate, the body height, and the age belong. The pathological conditions like arteriosclerosis or diabetes can change the arterial elasticity. Hypertension or some heart diseases influence the PW velocity.

As will be understood by those skilled in the art, the present invention may be embodied in other specific forms without departing from the essential characteristics thereof. Many other embodiments are possible without departing from the essential characteristics thereof. Many other embodiments are possible without deviating from the spirit and scope of the invention. These other embodiments are intended to be included within the scope of the present invention, which is set forth in the following claims.

What is claimed is:

1. A physiological information measuring apparatus comprising:
   a first detection unit, comprising a first light emitting unit and a first light receiving unit, wherein the first light emitting unit and the first light receiving unit are separated from one another by a first distance;
   a second detection unit, comprising a second light emitting unit and a second light receiving unit, wherein the second light emitting unit and the second light receiving unit are separated from one another by a second distance, different than the first distance; and
   a measuring unit that measures the physiological information of a user based on light received by the first light receiving unit and light received by the second light receiving unit,
   wherein wavelengths of the first light emitting unit and the second light emitting unit are approximately 470 nm to approximately 610 nm, and
   wherein the first distance is from approximately 2 mm to approximately 4 mm.

2. The apparatus according to claim 1, wherein the second distance is from approximately 4 mm to approximately 10 mm.

3. The apparatus of claim 1, wherein the first light emitting unit, the first light receiving unit, the second light emitting unit, and the second light receiving unit are disposed on an exposed surface of the apparatus and configured to contact skin of the user during use.

4. The apparatus of claim 1, wherein the first light receiving unit and the second light receiving unit are configured to apply pressure to the user.

5. The apparatus according to claim 1, wherein a first region from the first light emitting unit to the first light receiving unit along the surface of the apparatus overlaps a second region from the second light emitting unit to the second light receiving unit along the surface of the apparatus.

6. The apparatus according to claim 1, wherein the measuring unit measures the heart rate by removing noise, wherein the noise is measured based on differences between the light received by the first light receiving unit and the light received by the second light receiving unit.

7. The apparatus according to claim 1, wherein the physiological information comprises at least one member of the group consisting of a heart rate of the user, a blood pressure of the user, a breathing rate of the user, and an autonomic balance of the user.

8. The apparatus according to claim 1, wherein a first region from the first light emitting unit to the first light receiving unit along the surface of the apparatus intersects a second region from the second light emitting unit to the second light receiving unit along the surface of the apparatus.

9. A physiological information measuring apparatus comprising:
   a first detection unit, comprising a first light emitting unit and a first light receiving unit, wherein the first light emitting unit and the first light receiving unit are separated from one another by a first distance;
   a second detection unit, comprising one member of the group consisting essentially of:
   a) a second light emitting unit and a second light receiving unit;
   b) a second light emitting unit and the first light receiving unit; and
   c) the first light emitting unit and a second light receiving unit;
   wherein the light emitting unit of the second detection unit and the light receiving unit of the second detection unit are separated from one another by a second distance, different than the first distance; and
   a measuring unit that measures the physiological information of a user based on light received by the light receiving unit or by the light receiving units,
   wherein a wavelength of the first light emitting unit is approximately 470nm to approximately 610 nm, and the first distance is from approximately 2 mm to approximately 4 mm.

10. The apparatus of claim 9, wherein the light emitting unit or units and the light receiving unit or units are disposed on an exposed surface of the apparatus and configured to contact skin of the user during use.

11. The apparatus of claim 9, wherein the light receiving unit or units are configured to apply pressure to the user.

12. The apparatus of claim 11, comprising the second light receiving unit, wherein the first light receiving unit is configured to apply an amount of pressure, and the second light receiving unit is configured to apply a substantially identical amount of pressure.

13. The apparatus according to claim 9, wherein the physiological information comprises at least one member of the group consisting of a heart rate of the user, a blood pressure of the user, a breathing rate of the user, and an autonomic balance of the user.

14. The apparatus according to claim 9, further comprising:
   a first region from the first light emitting unit to the first light receiving unit along the surface of the apparatus intersects a second region from the second light emitting unit to the second light receiving unit along the surface of the apparatus.

* * * * *